(12) United States Patent
Yao

(10) Patent No.: US 8,765,990 B2
(45) Date of Patent: Jul. 1, 2014

(54) COMPOUND, RESIN COMPOSITION, AND RESIN MOLDED ARTICLE

(75) Inventor: Kenji Yao, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 541 days.

(21) Appl. No.: 13/206,051

(22) Filed: Aug. 9, 2011

(65) Prior Publication Data

US 2012/0204755 A1 Aug. 16, 2012

(30) Foreign Application Priority Data

Feb. 10, 2011 (JP) ................................. 2011-027702

(51) Int. Cl.
| | |
|---|---|
| *C08K 5/12* | (2006.01) |
| *C08L 11/00* | (2006.01) |
| *C08L 31/00* | (2006.01) |
| *C08L 77/00* | (2006.01) |
| *C07C 69/96* | (2006.01) |

(52) U.S. Cl.
CPC . *C08K 5/12* (2013.01); *C08L 11/00* (2013.01); *C08L 31/00* (2013.01); *C08L 77/00* (2013.01); *C07C 69/96* (2013.01); *C07C 2101/16* (2013.01)
USPC .......................... 558/266; 106/18.11; 524/289

(58) Field of Classification Search
CPC ........... C08K 5/12; C08L 11/00; C08L 31/00; C08L 77/00; C07C 69/96; C07C 2101/16
USPC .......................... 106/18.11; 524/289; 558/266
See application file for complete search history.

(56) References Cited

U.S. PATENT DOCUMENTS

| | | | | |
|---|---|---|---|---|
| 5,462,450 | A | * | 10/1995 | Kodama ....................... 439/489 |
| 5,581,266 | A | * | 12/1996 | Peng et al. ................... 343/770 |
| 7,498,422 | B2 | * | 3/2009 | Yao ............................... 530/502 |
| 7,598,305 | B2 | * | 10/2009 | Yao ................................. 524/74 |
| 7,598,319 | B2 | * | 10/2009 | Yao ............................. 525/54.21 |
| 8,563,633 | B2 | * | 10/2013 | Kawashima et al. ........... 524/72 |
| 2011/0294928 | A1 | * | 12/2011 | Nodera et al. ................. 524/73 |

FOREIGN PATENT DOCUMENTS

| | | |
|---|---|---|
| JP | A-2001-64494 | 3/2001 |
| JP | B2-3632763 | 3/2005 |

* cited by examiner

*Primary Examiner* — David M Brunsman
(74) *Attorney, Agent, or Firm* — Oliff PLC

(57) ABSTRACT

Disclosed is a compound represented by formula (1):

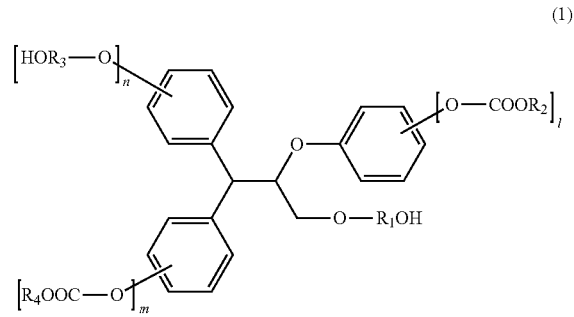

(1)

wherein $R_1$ and $R_3$ each independently represent an alkylene group having 1 to 10 carbon atoms or an arylene group; $R_2$ and $R_4$ each independently represent a hydrogen atom, an alkyl group having 1 to 6 carbon atoms, or an aryl group; and l, n and m each independently represent a natural number of 1 to 3.

18 Claims, 2 Drawing Sheets

COMPOUND, RESIN COMPOSITION, AND RESIN MOLDED ARTICLE

CROSS-REFERENCE TO RELATED APPLICATIONS

This application is based on and claims priority under 35 USC 119 from Japanese Patent Application No. 2011-027702 filed Feb. 10, 2011.

BACKGROUND

1. Technical Field

The present invention relates to a compound, a resin composition and a resin molded article.

2. Related Art

Conventionally, a variety of resin compositions have been provided and used for various applications. In particular, thermoplastic resins are used for various components such as cases for home appliances or automobiles, office equipment, and electric and electrical devices.

SUMMARY

According to an aspect of the invention, there is provided a compound represented by formula (1).

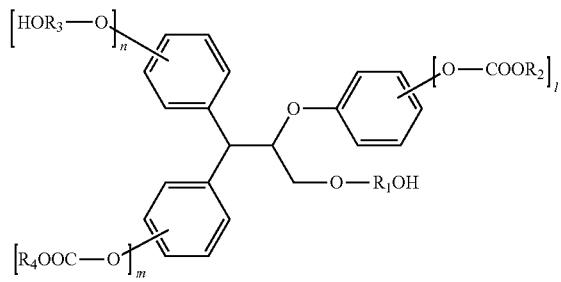

In formula (1), $R_1$ and $R_3$ each independently represent an alkylene group having 1 to 10 carbon atoms or an arylene group, $R_2$ and $R_4$ each independently represent a hydrogen atom, an alkyl group having 1 to 6 carbon atoms, or an aryl group, and l, n and m each independently represent a natural number of 1 to 3.

BRIEF DESCRIPTION OF THE DRAWINGS

Exemplary embodiments of the present invention will be described in detail based on the following figures, wherein.

DETAILED DESCRIPTION

Figure 1:
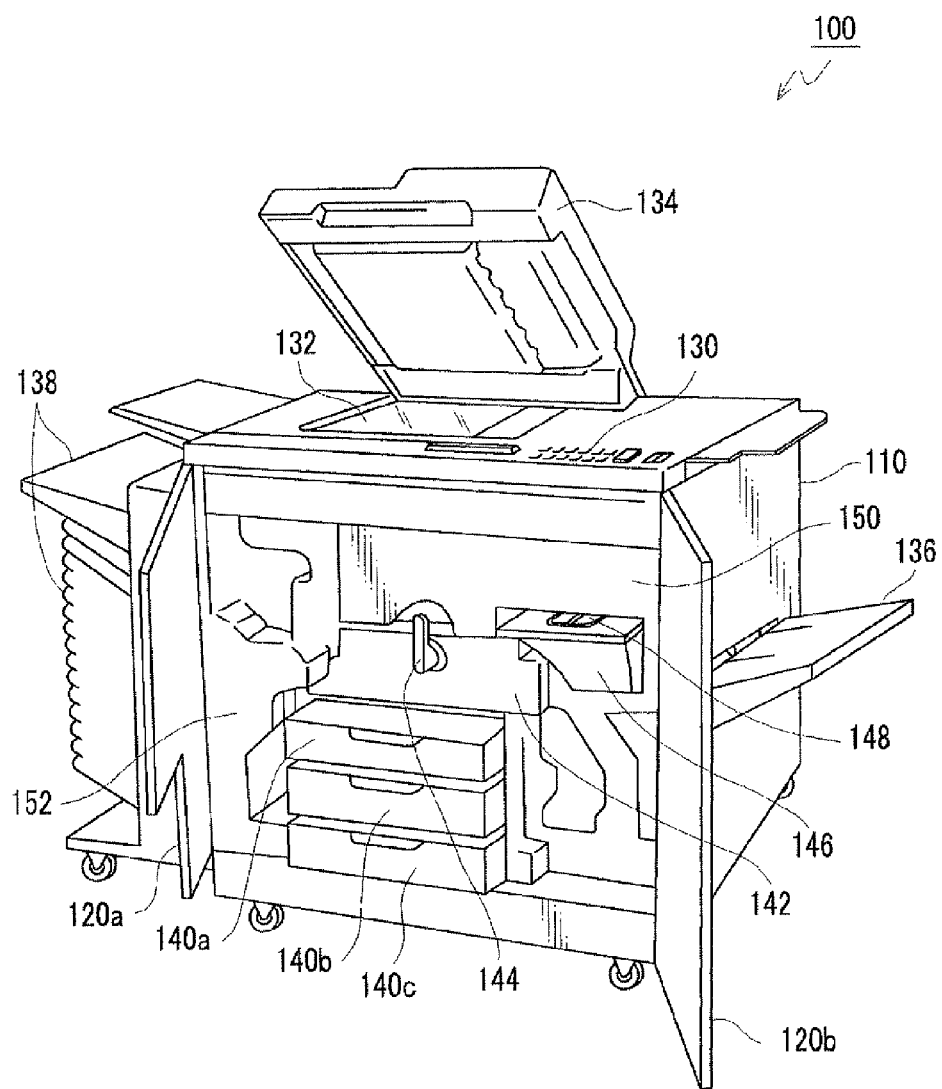
FIG. 1 is a schematic view illustrating an example of a component of an electronic and electrical device including a resin molded article related to this exemplary embodiment.

Hereinafter, exemplary embodiments of a compound, resin composition and resin molded article according to the present invention will be described.

[Compound]

The compound related to this exemplary embodiment is a multifunctional compound represented by formula (1). The multifunctional compound represented by the following formula (1) is a novel compound which imparts flame retardancy to resins.

The reason is not clear, but is presumed that a benzene ring and a carboxyl (ester thereof) group in a molecular structure of the multifunctional compound represented by formula (1) interact by combustion to form carbonized layers similar to carbonate resins.

Hereinafter, the multifunctional compound represented by formula (1) will be described in detail.

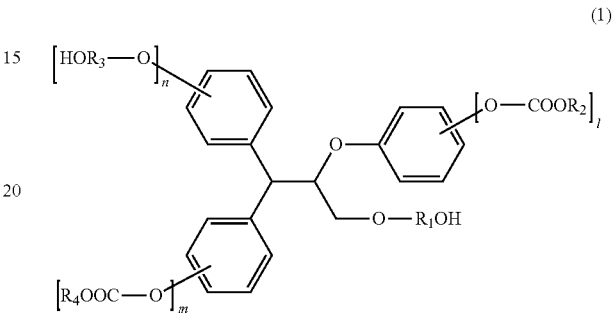

In formula (1), $R_1$ and $R_3$ each independently represent an alkylene group having 1 to 10 carbon atoms, or an arylene group. $R_2$ and $R_4$ each independently represent a hydrogen atom, an alkyl group having 1 to 6 carbon atoms, or an aryl group. l, n and m each independently represent a natural number of 1 to 3.

In formula (1), the alkylene group having 1 to 10 carbon atoms represented by $R_1$ and $R_3$ may be a straight or branched chain, and specific examples thereof include a methylene group, an ethylene group, an n-propylene group, an isopropylene group (methylethylene group), an n-butylene group, an isobutylene group, a sec-butylene group, a tert-butylene group, a pentylene group, a hexylene group, an octylene group and the like.

The alkylene group having 1 to 10 carbon atoms is preferably an alkylene group having 1 to 6 carbon atoms, more preferably an alkylene group having 1 to 4 carbon atoms.

The arylene group represented by $R_1$ and $R_3$ may be one selected from a phenylene group and a naphthylene group.

The arylene group is preferably an arylene group having 6 to 14 carbon atoms, more preferably an arylene group having 6 to 10 carbon atoms.

In formula (1), the alkyl group having 1 to 6 carbon atoms represented by $R_2$ and $R_4$ may be straight or branched chain and, specifically, the alkyl group having 1 to 6 carbon atoms represented by $R_2$ and $R_4$ may be one selected from a methyl group, an ethyl group, an n-propyl group, an isopropyl group (methylethyl group), an n-butyl group, an isobutyl group, a sec-butyl group, a tert-butyl group, a pentyl group and a hexyl group.

The alkyl group having 1 to 6 carbon atoms is preferably an alkyl group having 1 to 4 carbon atoms, more preferably an alkyl group having 1 to 3 carbon atoms.

The aryl group represented by $R_2$ and $R_9$ in formula (1) may be one selected from a phenyl group and a naphthyl group.

The aryl group is preferably an aryl group having 6 to 14 carbon atoms, more preferably an aryl group having 6 to 10 carbon atoms.

The group represented by each symbol in formula (1) includes substituted or un-substituted groups and examples of groups which may be a substituent of these groups include an alkyl group having 1 to 10 carbon atoms, an aryl group and the like.

In formula (1), l, n and m each independently represent a natural number of 1 to 3 and preferably a natural number of 1 or 2.

Here, the compound represented by formula (1) is preferably a compound wherein $R_1$ represents an alkylene group having 1 to 6 carbon atoms, $R_3$ represents an alkylene group having 1 to 6 carbon atoms, $R_2$ represents an alkyl group having 1 to 6 carbon atoms, $R_4$ represents an alkyl group having 1 to 6 carbon atoms, l represents a natural number of 1 to 3, n represents a natural number of 1 to 3 and m represents a natural number of 1 to 3.

In addition, the compound represented by formula (1) is particularly preferably a compound wherein $R_1$ represents an ethylene group or an n-butylene group, $R_3$ represents an ethylene group or an n-butylene group, $R_2$ represents a methyl group, $R_4$ represents a methyl group, l represents 1 or 2, n represents 1 or 2 and m represents 1 or 2.

Hereinafter, specific examples of the compound represented by formula (1) include, but are not limited to, the following compounds.

Hereinafter, a method for synthesizing the compound represented by formula (1) will be described.

Examples of the synthetic method for the compound represented by formula (1) include methods for synthesizing (inducing) the compound from a wood resource, lignin, as a starting material and other chemical synthesis methods. Particularly preferred is synthesis (induction) from a wood resource, lignin, used as a starting material, in that it is advantageous in terms of environmental load and expression of flame retardancy.

The method for synthesizing (inducing) the compound from a wood resource, lignin, is for example a method described in JP-A-2001-64494.

Specifically, lignophenol derivatives are obtained from a wood powder, dissolved in a solvent such as acetone, dicarbonic acid ester or hydroxycarboxylic acid ester having the desired structure is dissolved in a solvent such as tetrahydrofuran, a catalyst such as tetrabutoxytitanate is added, the two solutions are mixed with each other, and the mixture is vigorously stirred with refluxing at 60° C. The solution is added dropwise to water. The obtained precipitate is the target compound.

| | Raw materials | $R_1$ | $R_2$ | $R_3$ | $R_4$ | n/ [—$OR_3OH$] bond position | m/ [—$OCOOR_4$] bond position | l/ [—$OCOOR_2$] bond position |
|---|---|---|---|---|---|---|---|---|
| Multifunctional compound 1 | Naturally derived | Ethylene group | Methyl group | Ethylene group | Methyl group | 1/4 position | 1/4 position | 1/4 position |
| Multifunctional compound 2 | Naturally derived | Methylene group | Methyl group | Methylene group | Methyl group | 1/4 position | 1/4 position | 1/4 position |
| Multifunctional compound 3 | Naturally derived | n-Propylene group | Methyl group | n-Propylene group | Methyl group | 1/4 position | 1/4 position | 1/4 position |
| Multifunctional compound 4 | Naturally derived | n-Butylene group | Methyl group | n-Butylene group | Methyl group | 1/4 position | 1/4 position | 1/4 position |
| Multifunctional compound 5 | Naturally derived | 2-Methylethylene group | Methyl group | 2-Methylethylene group | Methyl group | 1/4 position | 1/4 position | 1/4 position |
| Multifunctional compound 6 | Naturally derived | n-Decamethylene group | Methyl group | n-Decamethylene group | Methyl group | 1/4 position | 1/4 position | 1/4 position |
| Multifunctional compound 7 | Naturally derived | Ethylene group | Methyl group | n-Butylene group | Methyl group | 1/4 position | 1/4 position | 1/4 position |
| Multifunctional compound 8 | Naturally derived | Phenylene group | Methyl group | Phenylene group | Methyl group | 1/4 position | 1/4 position | 1/4 position |
| Multifunctional compound 9 | Naturally derived | Ethylene group | Methyl group | Phenylene group | Methyl group | 1/4 position | 1/4 position | 1/4 position |
| Multifunctional compound 10 | Naturally derived | Naphthylene group | Methyl group | Naphthylene group | Methyl group | 1/4 position | 1/4 position | 1/4 position |
| Multifunctional compound 11 | Naturally derived | Ethylene group | n-Hexyl group | Ethylene group | n-Hexyl group | 1/4 position | 1/4 position | 1/4 position |
| Multifunctional compound 12 | Naturally derived | Ethylene group | tert-Butyl group | Ethylene group | tert-Butyl group | 1/4 position | 1/4 position | 1/4 position |
| Multifunctional compound 13 | Naturally derived | Ethylene group | Phenyl group | Ethylene group | Phenyl group | 1/4 position | 1/4 position | 1/4 position |
| Multifunctional compound 14 | Naturally derived | Ethylene group | Methyl group | Ethylene group | Phenyl group | 1/4 position | 1/4 position | 1/4 position |
| Multifunctional compound 15 | Naturally derived | Ethylene group | Methyl group | Ethylene group | Methyl group | 2/2, 6 position | 2/2, 6 position | 1/4 position |
| Multifunctional compound 16 | Naturally derived | Ethylene group | Methyl group | Ethylene group | Methyl group | 2/2, 6 position | 2/2, 6 position | 2/2, 6 position |
| Multifunctional compound 17 | Naturally derived | Ethylene group | Methyl group | Ethylene group | Methyl groups | 3/2, 4, 6 position | 2/2, 6 position | 2/2, 6 position |
| Multifunctional compound 18 | Naturally derived | Ethylene group | Methyl group | Ethylene group | Methyl group | 2/2, 6 position | 3/2, 4, 6 position | 2/2, 6 position |
| Multifunctional compound 19 | Naturally derived | Ethylene group | Methyl group | Ethylene group | Methyl group | 3/2, 4, 6 position | 3/2, 4, 6 position | 3/2, 4, 6 position |
| Multifunctional compound 20 | Naturally derived | Ethylene group | Methyl group | n-Butylene group | Phenyl group | 2/2, 6 position | 2/2, 6 position | 2/2, 6 position |
| Multifunctional compound 21 | Chemically synthesized | Ethylene group | Methyl group | Ethylene group | Methyl group | 1/4 position | 1/4 position | 1/4 position |

Meanwhile, another chemical synthesis is for example carried out in accordance with the described method using phenol derivative monomers (commercially available) having a structure similar to lignophenol derivatives.

[Resin Composition]

The resin composition related to this exemplary embodiment contains a resin and the compound represented by formula (1), and optionally contains a flame retardant, other ingredients or the like.

(Resin)

First, the resin will be described.

Examples of the resin include conventionally known thermoplastic resins and specific examples thereof include polycarbonate resins, polypropylene resins, polyamide resins, polylactic acid resins, aliphatic polyester resins, aromatic polyester resins, polyolefin resins, polyester carbonate resins, polyphenylene ether resins, polyphenylene sulfide resins, polysulfone resins, polyether sulfone resins, polyarylene resins, polyetherimide resins, polyacetal resins, polyvinyl acetal resins, polyketone resins, polyether ketone resins, polyether ether ketone resins, polyaryl ketone resins, polyether nitrile resins, liquid crystal resins, polybenzimidazole resins, polyparabanic acid resins, aromatic alkenyl compounds, methacrylic acid esters, acrylic acid esters, vinyl-based polymer or copolymer resins obtained by polymerizing or copolymerizing one or more vinyl monomers selected from the group consisting of vinyl cyanide compounds, diene-aromatic alkenyl compound copolymer resins, vinyl cyanide-diene-aromatic alkenyl compound copolymer resins, aromatic alkenyl compound-diene-vinyl cyanide-N-phenyl maleimide copolymer resins, vinyl cyanide-(ethylene-diene-propylene (EPDM))-aromatic alkenyl compound copolymer resins, polyolefins, vinyl chloride resins, chlorinated vinyl chloride resins and the like.

These resins may be used alone or in combination of two or more types.

Of these resins, aliphatic polyester resins, aliphatic polyamide resins and cellulose resins are preferred.

When the aliphatic polyester resin is used, the resin composition can exhibit flame retardancy through a small amount (for example about 1/10 of conventional flame retardants) of the compound represented by formula (1). The reason is not clear, but it is presumed that the compound represented by formula (1) is homogeneously dispersed with ease in the aliphatic polyester resin.

In addition, the homogeneous dispersion is thought to be caused by a reaction of the compound represented by formula (1) with the end of the aliphatic polyester resin. As a result, the resin composition is thought to exhibit hydrolysis resistance.

When the aliphatic polyamide resin is used, the obtained resin molded article exhibits an improved elastic modulus. The reason is not clear, but it is presumed that affinity between the end group of the aliphatic polyamide resin and the compound represented by formula (1) is high and molecular motion for the aliphatic polyamide resin having a generally low elastic modulus is limited.

In addition, it is thought that, when the molecular motion of the aliphatic polyamide resin is excessively limited, bending fracture distortion tends to decrease, but the molecular motion and intermolecular force of the aliphatic polyamide resin is suitably limited and bending fracture distortion of the obtained resin molded article is thus improved, since the molecular size of the compound represented by formula (1) is relatively suitable.

In addition, molecules are constricted and temperature-dependency of molecular motion (generally, as temperatures increase, molecules more readily move) thus is thought to be decreased. As a result, the obtained resin molded article can exhibit heat resistance.

When cellulose resin is used, the obtained resin molded article exhibits improved dimensional stability. The reason is not clear, but is thought that at least one of hydroxyl and alkoxy groups of cellulose resin which has superior absorbency and large dimensional variation during storage when it is formed into resin molded articles reacts with the compound represented by formula (1) having a relatively suitable molecular size to block hydroxyl and alkoxy groups contributing to absorbency.

In addition, the compound represented by formula (1) has high reactivity with cellulose and has a chemical structure in which hard segments such as phenylene rings and soft segments such as olefin or ether are present with a relatively short cycle, thus strength in a ball drop test may be improved.

Hereinafter, a case where an aliphatic polyester resin is applied will be described in detail.

Examples of aliphatic polyester resins include hydroxycarboxylic acid polymers, condensates of aliphatic diol and aliphatic carboxylic acid and the like.

These resins may be used alone or in combination of two or more.

Of these aliphatic polyester resins, hydroxycarboxylic acid polymers (such as polylactic acid, polyhydroxybutyrate, polyhydroxyadipate, polyhydroxyhexanoate, polyhydroxyvalerate and copolymers thereof) are preferred. In particular, of hydroxycarboxylic acid polymers, polylactic acid and polyhydroxy butyrate are preferred.

The aliphatic polyester resin may be any condensate of lactic acid (for example, polyhydroxy butyrate). The polylactic acid may be present as a mixture or optical isomers such as L-polylactic acid and D-polylactic acid, or a copolymer thereof.

The weight average molecular weight of the aliphatic polyester resin is not particularly limited, and is for example from 8,000 to 150,000 and preferably from 20,000 to 100,000.

When the weight average molecular weight is lower than this range, it is difficult to improve crosslink density, when the aliphatic polyester resin reacts with the compound of formula (1) and thus forms cross-linkages. When the weight average molecular weight exceeds this range, cross-linking reactivity between the aliphatic polyester resin and the compound of formula (1) tends to decrease.

The weight average molecular weight is a value measured by using a gel permeation chromatography system (Prominence GPC manufactured by Shimadzu Corporation) using a Shim-pack GPC-80M as a test column. This is also applied to the following.

The aliphatic polyester resin and the compound which represented by formula (1) react with each other and form a cross-linked structure and may be contained in the resin composition (resin molded article), or they do not react each other and may be contained in the resin composition (resin molded article). From the viewpoint of improving flame retardancy, it is preferred that the aliphatic polyester resin and the compound represented by formula (1) react with each other and form a cross-linked and be contained in the resin composition (resin molded article).

When the aliphatic polyester resin and the compound represented by formula (1) react with each other and form a cross-linked structure, an end capping degree of the aliphatic polyester resin of the compound represented by formula (1) is preferably 0.5 or more, and more preferably 0.8 or more and 0.95 or less.

The end capping degree of the aliphatic polyester resin is defined as a ratio of the number of capped ends to the number of uncapped ends among aliphatic polyester ends present (the number of capped ends/the number of uncapped ends) and is obtained by measuring intensity ratios of peaks corresponding to respective ends using FT-IR (JASCO, FT/IR-6000) and comparing the values.

Here, a ratio of a mass (A) of the compound represented by formula (1) and a mass (B) of the aliphatic polyester resin {(A)/(B)} is not limited and is for example 0.05/100 to 1.5/100, preferably 0.1/100 to 1/100.

When the compound and the aliphatic polyester resin are contained at a ratio lower than this range in the resin composition, flame retardancy tends to deteriorate, and when they are contained at a ratio higher than this range in the resin composition, flowability and moldability tend to deteriorate.

Hereinafter, a case where an aliphatic polyamide resin is applied will be described in detail.

The aliphatic polyamide resin is not particularly limited and examples thereof include polyamide 6, polyamide 6-6, polyamide 4-6, polyamide 6-10, polyamide 6-12, polyamide 11, polyamide 12, polyamide 9-10, polyamide 9-12, polyamide 9-13, polyamide 9-14, polyamide 9-15, polyamide 6-16, polyamide 9-36, polyamide 10-10, polyamide 10-6, polyamide 10-12, polyamide 10-13, polyamide 10-14, polyamide 12-10, polyamide 12-12, polyamide 12-13, polyamide 12-14, polyamide 6-14, polyamide 6-13, polyamide 6-15, polyamide 6-16, polyamide 6-13 and the like.

These resins may be used alone or in combination of two or more.

Of the aliphatic polyamide resins, polyamide 11, polyamide 10-10 and polyamide 10-6 are preferred from a viewpoint of improving an elastic modulus and bending fracture distortion of the obtained resin molded article.

In addition, from a viewpoint of improving of heat resistance of the obtained resin molded article, the aliphatic polyamide resin is preferably prepared from materials derived from plants.

The weight average molecular weight of the aliphatic polyamide resin is not particularly limited and is for example 5,000 to 200,000, preferably 10,000 to 150,000.

When the weight average molecular weight is lower this range, the bending fracture distortion of the obtained resin molded article tends to deteriorate, and when the weight average molecular weight exceeds this range, the elastic modulus of the obtained resin molded article tends to deteriorate.

The aliphatic polyamide resin and the compound represented by formula (1) react with each other and form a cross-link structure and may be contained in the resin composition (resin molded article), or they do not react with each other and may be contained in the resin composition (resin molded article). From the viewpoint of improving the elastic modulus and bending fracture distortion of the obtained resin molded article, it is preferable that the aliphatic polyamide resin and the compound represented by formula (1) react with each other and form a cross-link structure and may be contained in the resin composition (resin molded article).

When the aliphatic polyamide resin and the compound represented by formula (1) react with each other and form a cross-link structure, an end capping degree of the aliphatic polyamide resin of the compound represented by formula (1) is preferably 0.5 or more, and more preferably 0.8 or more and 0.95 or less.

In addition, the end capping degree of the aliphatic polyamide resin is defined as a ratio of the number of capped ends to the number of uncapped ends among aliphatic polyamide ends present, (the number of capped ends/the number of uncapped ends) and is obtained by measuring an intensity ratios of peaks corresponding to respective ends using FT-IR (JASCO, FT/IR-6000) and comparing the measured values.

Here, a ratio of a mass (A) of the compound represented by formula (1) and a mass (B) of the aliphatic polyamide resin {(A)/(B)} is not limited and is for example 0.05/100 to 5/100, preferably 0.1/100 to 3/100.

When the compound and the aliphatic polyamide resin are contained at a ratio lower than this range in the resin composition, it is difficult to improve an elastic modulus of the obtained resin molded article, and when they are contained at a ratio higher than this range in the resin composition, bending fracture distortion of the obtained resin molded article tends to deteriorate.

Hereinafter, a case where a cellulose resin is applied will be described in detail.

Examples of the cellulose resin include unsubstituted cellulose, hemicellulose, substituted cellulose (cellulose with substituent acetyl groups, n-propoxyl groups, iso-propoxyl groups, n-butoxyl groups, iso-butoxyl groups, tert-butoxyl groups) and the like.

These resins may be used alone or in combination of two or more.

Of these cellulose resins, from the viewpoint of improving dimensional stability of the obtained resin molded article, substituted and unsubstituted celluloses, substituted celluloses (such as diacetyl cellulose, triacetyl cellulose, carboxymethyl cellulose, cellulose acetate propionate (=acetyl-propyl-cellulose)) substituted with substituent groups having a relatively small molecular weight (such as acetyl groups, alkyl groups having 1 to 3 carbon atoms, carboxyl groups) are preferable.

The weight average molecular weight of the cellulose resin is not particularly limited and is for example from 8,000 to 200,000, preferably from 15,000 to 100,000.

In addition, the number average molecular weight of the cellulsose resin is not particularly limited and is for example from 4,000 to 150,000, preferably from 8,000 to 100,000.

When these average molecular weights are lower than the respective ranges, mechanical strength tends to deteriorate, and when these average molecular weights exceed the respective ranges, moldability tends to deteriorate.

In addition, the molecular weight distribution of the cellulose resin (weight average molecular weight Mw/number average molecular weight Mn) is for example 3 to 8, preferably 3.5 to 5.

When the molecular weight distribution is lower than this range, moldability tends to deteriorate and when the molecular weight distribution exceeds this range, mechanical strength tends to deteriorate.

The cellulose resin and the compound represented by formula (1) react with each other and form a cross-link structure and may be contained in the resin composition (resin molded article).

Here, a ratio of a mass (A) of the compound represented by formula (1) and a mass (B) of the cellulose resin {(A)/(B)} is not limited and is for example 0.5/100 to 10/100, preferably 1/100 to 5/100.

When the compound and the cellulose resin are contained at a ratio lower than this range in the resin composition, it is difficult to improve dimensional stability of the obtained resin molded article, and when they are contained at a ratio higher than this range in the resin composition, dimensional stability of the obtained resin molded article tends to deteriorate.

In addition, the content of all resins in the resin composition related to this exemplary embodiment is preferably for example 50% by mass to 95% by mass or less, based on the total amount of the resin composition.

(Flame Retardant)

Examples of the flame retardant include phosphorus-based, silicone-based, nitrogen-based, sulfate-based and metal hydroxide-based flame retardants.

Examples of the phosphorus-based flame retardant include condensed ester phosphate, melamine polyphosphate, ammonium polyphosphate, aluminum polyphosphate, melamine pyrophosphate and the like.

Examples of the silicon-based flame retardant include dimethylsiloxane, nano silica, silicone-modified polycarbonate and the like.

Examples of the nitrogen-based flame retardant include melamine compounds, triazine compounds and the like.

Examples of the sulfate-based flame retardant include melamine sulfate, guanidine sulfate and the like.

Examples of inorganic hydroxide-based flame retardant include magnesium hydroxide, aluminum hydroxide, montmorillonite and the like.

Of these flame retardants, from the viewpoint of improving flame retardancy, phosphorus-based, sulfate-based, and inorganic hydroxide-based flame retardants are preferred, and in particular, flame retardants present in a solid state at room temperature (for example, 25° C.), such as, melamine polyphosphate, ammonium polyphosphate, aluminum polyphosphate, melamine pyrophosphate, magnesium hydroxide, aluminum hydroxide, and montmorillonite are preferred.

In addition, the flame retardant may be selected from synthesized or commercially available products.

Examples of commercially available phosphorus-based flame retardant products include PX-200 and PX-202 (trade names, manufactured by Daihachi Chemical Industry Co., Ltd.), TERRAJU C80 (trade name, manufactured by Chemische Fabrik Budenheim KG), and EXOLIT AP422 and EXOLIT OP930 (trade names, manufactured by Clariant AG).

Examples of commercially available silicone-based flame retardant products include DC4-7081 (trade name, manufactured by Dow Corning Toray Co., Ltd.).

Examples of commercially available nitrogen-based flame retardant products include FP2200 (trade name, manufactured by ADEKA CORPORATION).

Examples of commercially available sulfate-based flame retardant products include APINON 901 (trade name, manufactured by Sanwa Chemical Co., Ltd.), melamine pyrophosphate manufactured by Shimonoseki Mitsui Chemicals, Inc., and FP2100 (trade name, manufactured by ADEKA CORPORATION).

Examples of commercially available inorganic-hydroxide-based flame retardant products include MGZ3 and MGZ300 (trade names, manufactured by Sakai Chemical Industry Co., Ltd.) and B103ST (trade name, manufactured by Nippon Light Metal Co., Ltd.).

The content of the flame retardant is for example 1% by mass to 50% by mass or less, preferably, 5% by mass to 20% by mass or less, based on the total amount of the resin composition.

(Other Ingredient)

Examples of the other ingredient include compatibilizers, plasticizers, antioxidants, releasing agents, light-resistant agents, anti-weathering agents, colorings, pigments, modifiers, anti-dripping agents, antistatic agents, anti-hydrolysis agents, fillers, reinforcing agents (glass fiber, carbon fibers, talc, clay, mica, glass flake, milled glass, glass beads, crystalline silica, alumina, silicon nitride, alumina nitride, boron nitride and the like.

The content of other ingredients is for example 0% by mass to 10% by mass, preferably 0% by mass to 5% by mass. Here, "0% by mass" means that the resin composition contains no other ingredients.

(Method for Preparing Resin Composition)

The resin composition related to this exemplary embodiment is prepared by melt-mixing the mixture of respective ingredients.

Here, a tool for melt-mixing may be any of those known in the art and examples thereof include biaxial extruders, Henschel mixers, Banbury mixers, monoaxial screw extruders, multi-axial screw extruders, co-kneaders and the like.

[Resin Molded Article]

The resin molded article related to this exemplary embodiment contains the resin composition related to this exemplary embodiment.

Specifically, the resin molded article related to this exemplary embodiment can be obtained by molding the resin composition related to this exemplary embodiment (by a molding method such as injection molding, extrusion molding, blow molding, heat press molding, calendar molding, coating molding, cast molding, dipping molding, vacuum molding and transfer molding).

The injection molding may be for example carried out using a commercially available apparatus such as NEX150 (manufactured by Nissei Resin Industry Co., Ltd.), NEX70000 (manufactured by Nissei Resin Industry Co., Ltd.), SE50D (manufactured by Toshiba Machine Co., Ltd.).

At this time, the cylinder temperature is preferably 170° C. to 280° C., more preferably 180° C. to 270° C. In addition, a molding temperature is preferably 40° C. to 110° C., more preferably 50° C. to 110° C.

The resin molded article related to this exemplary embodiment is suitable for use in applications including electric and electrical devices, home appliances, containers, interior materials for automobiles and the like. More specifically, the resin molded article is suitable for cases of home appliances, electric and electrical devices and the like, a variety of components and the like, wrapping films, storage cases for CD-ROMs, DVDs and the like, dishes, food trays, drink bottles, pharmaceutical packaging and the like. Of these, components of electric and electrical devices are suitable as intended use.

FIG. 1 is a front perspective view illustrating the outer appearance of an image forming apparatus, as one example of components electric and electrical devices including the molded article related to this exemplary embodiment.

The image forming apparatus 100 of FIG. 1 includes a body 110 and front covers 120a and 120b arranged at the front side of the body 110. These front covers 120a and 120b may open and close to enable an operator to perform operations in the apparatus. The operator can refill used toner, replace a used-up process cartridge with a new one and remove paper jammed in the apparatus through the front covers 120a and 120b. FIG. 1 shows an apparatus in which the front covers 120a and 120b are open.

The body 110 is provided on the top surface thereof with an operating panel 130 to enable an operator to input terms and conditions associated with image formation such as paper size or number of copies and a copy glass 132 on which a manuscript to be read is arranged. In addition, the body 110 is provided on the top thereof with an automatic manuscript transport device 134 to transport the manuscript onto the copy glass 132. In addition, the body 110 includes an image reader to scan a manuscript image arranged on the copy glass 132 and thereby obtain image data representing the manuscript image. The image data obtained by the image reader is transferred through a controlling unit to an image forming unit. In addition, the image reader and the controlling unit are accommodated in a case 150 constituting a part of the body 110. In addition, the image forming unit is provided as a detachable process cartridge 142 in the case 150. The detachment of the process cartridge 142 can be accomplished by turning an operating lever 144.

The case 150 of the body 110 is provided with a toner accommodating unit 146 and a toner is replenished from a toner supply hole 148. The toner accommodated in the toner accommodating unit 146 is supplied to a developing unit.

Meanwhile, the body 110 is provided in lower parts thereof with paper storage cassettes 140a, 140b and 140c. In addition, plural transport rollers including a pair of rollers are arranged in the body 110, thus forming a transport passage in which the paper is carried from the paper storage cassettes to the image forming unit arranged thereon. In addition, paper of each paper storage cassette is supplied one piece at a time through a paper supply device arranged near the end of the transport passage and transferred to the transport passage. In addition, the body 110 is provided at the side thereof with a manual paper feed unit 136, through which paper is also supplied.

The paper on which an image is formed by the image forming unit is transported between two fixing rollers which contact each other supported by the case 152 constituting a part of the body 110 and discharged outside the body 110. The body 110 has one side in which the paper supply unit 136 is provided and an opposite side in which plural paper discharge units 138 are provided. After image formation, paper is discharged through the paper discharge unit.

The resin molded article related to this exemplary embodiment is for example used for the front covers 120a and 120b, exterior material of the process cartridge 142, the case 150 and the case 152 in the image forming apparatus 100.

EXAMPLES

The present invention will be described with reference to the following examples in detail, but is not limited thereto. In addition, the following "part" is based on mass, unless specifically described otherwise.

[Synthesis of Compound 1]
(Multifunctional Compound 1)
—Synthesis—

A waste material of Hinoki (Chamaecyparis obtuse) is screened through a 20 mesh sieve, 10 parts by mass of chips passing through the sieve is dipped in acetone for 20 hours, vacuum-dried at 80° C. for 8 hours and degreased. After degreasing, 50 parts by mass of p-cresol is added to the degreased chips, the mixture is stirred at room temperature for 4 hours, followed by adding 50 parts by mass of 78% concentrated sulfuric acid and stirring at 30° C. for one hour. Then, 1000 parts by mass of distilled water is added and the mixture is stirred and an upper layer is separated and removed by decantation. A lower layer is dissolved in diethyl ether, acetone is added thereto, a diethyl ether layer is extracted in a separating funnel, and the extraction is reprecipitated in distilled water. 1 part by mass of ethylene glycol, 2 parts by mass of methyl acetate, and 0.01 part by mass of tetrabutoxytitanium are added to 5 parts by mass of this precipitate and the mixture is stirred at 140° C. under a vacuum atmosphere for 6 hours to obtain a multifunctional compound 1.

Through the treatment described above, the multifunctional compound 1 is pelletized.

—Identification—

The multifunctional compound 1 thus obtained is identified as follows.

Measurement of IR Spectrum.

In a spectrum, characteristic peaks of a basic skeleton of lignocresol are observed at 1 (at the vicinity of 1,098 $cm^{-1}$) and 2 (at the vicinity of 1,595 $cm^{-1}$), which indicates presence of a lignocresol skeleton. In addition, a terminal esterified carbonyl structure is confirmed from intense peaks of 3 (at the vicinity of 1,750 $cm^{-1}$) and a terminal hydroxylethyl structure is confirmed from a peak intensity of 3,000 $cm^{-1}$ or higher in 4 (at the vicinity of 2,980 $cm^{-1}$), which indicates that presence of the multifunctional compound 1.

As apparent from the foregoing, the obtained compound is identified as the multifunctional compound 1.

Figure 2:
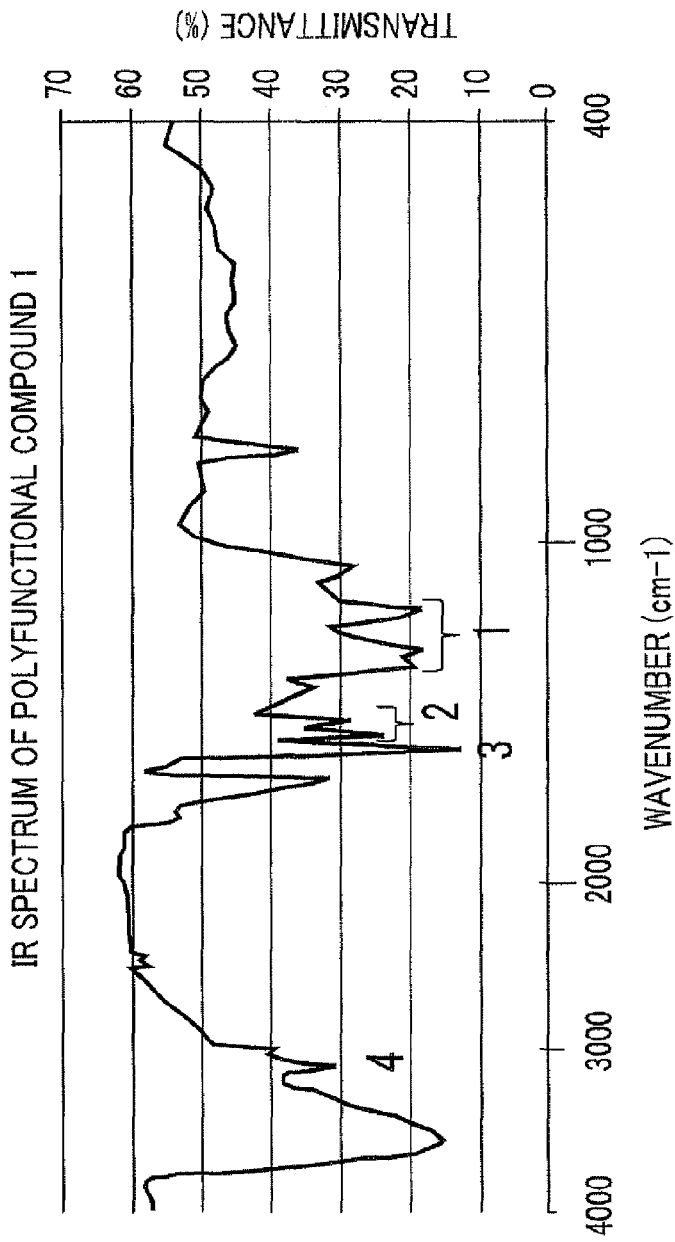
FIG. 2 is a view illustrating an IR spectrum of a multifunctional compound 1.

In addition, FIG. 2 shows an IR spectrum of the multifunctional compound 1.

(Multifunctional Compound 21)
—Synthesis—

7 parts by mass of phenol, 3 parts by mass of ethylene glycol and 100 parts by mass of tetrahydrofuran are added to 10 parts by mass of commercially available diphenyl ethene (manufactured by Wako Pure Chemical Industries Ltd.), followed by stirring at 40° C., to obtain a homogeneous solution. 0.05 part by mass of azoisobutyronitrile is added to the solution, followed by stirring with refluxing at 100° C. for 30 hours. The obtained solution is reprecipitated in distilled water and filtered to obtain a precipitate. 1 part by mass of ethylene glycol, 2 parts by mass of methyl acetate, and 0.01 part by mass of tetrabutoxytitanium are added to 5 parts by mass of this precipitate and the mixture is stirred at 140° C. under a vacuum atmosphere for 6 hours to obtain a multifunctional compound 21.

Through the treatment described above, the multifunctional compound 21 is pelletized.

Examples A1 to A21 and Comparative Example A1

In accordance with Table 1, respective multifunctional compounds (the compound represented by formula (1)) are pressed using a single acting press and cut into UL test specimens (thickness 2 mm) in accordance with UL-94 to manufacture test specimens.

In addition, as Comparative compound 1 (Comparative Example A1), a lignophenol derivative obtained with a method described in Japanese Patent No. 3632763 is treated in the same manner as described above to manufacture test specimens.

In addition, the obtained test specimens are flame-welded using a UL-94 V test method, and the flame retardancy of compounds is evaluated from a combustion period during primary flame welding. The results thus obtained are shown in Table 1.

TABLE 1

| | Type of compound | Combustion period sec |
|---|---|---|
| Ex. A1 | Multifunctional compound 1 | 14 |
| Ex. A2 | Multifunctional compound 2 | 12 |
| Ex. A3 | Multifunctional compound 3 | 10 |
| Ex. A4 | Multifunctional compound 4 | 15 |
| Ex. A5 | Multifunctional compound 5 | 10 |
| Ex. A6 | Multifunctional compound 6 | 12 |
| Ex. A7 | Multifunctional compound 7 | 10 |
| Ex. A8 | Multifunctional compound 8 | 12 |
| Ex. A9 | Multifunctional compound 9 | 14 |
| Ex. A10 | Multifunctional compound 10 | 14 |
| Ex. A11 | Multifunctional compound 11 | 13 |
| Ex. A12 | Multifunctional compound 12 | 14 |
| Ex. A13 | Multifunctional compound 13 | 12 |

TABLE 1-continued

|  | Type of compound | Combustion period sec |
|---|---|---|
| Ex. A14 | Multifunctional compound 14 | 12 |
| Ex. A15 | Multifunctional compound 15 | 14 |
| Ex. A16 | Multifunctional compound 16 | 13 |
| Ex. A17 | Multifunctional compound 17 | 12 |
| Ex. A18 | Multifunctional compound 18 | 15 |
| Ex. A19 | Multifunctional compound 19 | 10 |
| Ex. A20 | Multifunctional compound 20 | 12 |
| Ex. A21 | Multifunctional compound 21 | 14 |
| Comp. Ex. A1 | Comparative compound 1 | 55 |

Example B

Examples B1 to B29 and Comparative Examples B1 to B7

The compositions shown in Tables 2 and 3 are mixed in a biaxial mixer (TEM58SS manufactured by Toshiba Machine Co., Ltd.) at a cylinder temperature of 180° C. to 200° C. to obtain a resin composition pellet.

In addition, in Tables 2 and 3, Comparative compound 1 is a lignophenol derivative obtained by a method described in Japanese Patent No. 3632763.

The obtained pellet is molded into ISO versatile dumbbell test specimens (corresponding to ISO527 tensile testing, in accordance with ISO178 bending test, test part thickness 4 mm, width 10 mm) and UL test specimens for UL-94 V testing (thickness: 0.8 mm, 1.6 mm) in an injection molding machine (NEX150 manufactured by Nissei Resin Industry Co., Ltd.) at a cylinder temperature of 180° C. to 200° C. at a molding temperature of 30° C.

(Evaluation)

The pellets and test specimens thus obtained are subjected to the following evaluation testing. The results thus obtained are shown in Tables 4 and 5.

—End Capping Degree—

An end capping degree of aliphatic polyester resin in the pellets is evaluated by FT-IR (JASCO, FT/IR-6000).

—Flame Retardancy—

A UL-V testing is performed in accordance with UL-94 using UL test specimens for V testing. In addition, evaluation bases are V0, V1 and V2 from high flame retardancy in this order and in a case where flame retardancy is lower than V2, that is, the test specimen is combusted, the level is represented by V-Not.

—Hydrolysis Resistance—

The IS178 bending test is performed before and after the ISO versatile dumbbell test specimens are left to stand at 65° C./85% RH for 2000 hours, to measure bending fracture distortion (INSTRON SV-50 manufactured by TOYO SEIKI Co., Ltd.). These values are evaluated as hydrolysis resistance. Suppression of deterioration of bending fracture distortion after standing for 2000 hours means presence of hydrolysis resistance,

TABLE 2

|  | Multifunctional compounds | | Aliphatic polyester resin | | | Flame retardant | | |
|---|---|---|---|---|---|---|---|---|
|  |  |  | Polylactic acid Terramac | Polyhydroxy alkanoate | Catalyst | Phosphorus-based | Sulfate-based APINON | Metal hydroxide ECOMAG |
|  | Type | Parts by mass | TE2000 Parts by mass | BIOPOLE Parts by mass | Tetrabutoxytitanium Parts by mass | PX200 Parts by mass | 901 Parts by mass | PZ-1 Parts by mass |
| Ex. B1 | Multifunctional compound 1 | 0.2 | 100 |  |  |  |  |  |
| Ex. B2 | Multifunctional compound 1 | 0.2 | 100 |  | 0.002 |  |  |  |
| Ex. B3 | Multifunctional compound 1 | 0.2 |  | 100 | 0.002 |  |  |  |
| Ex. B4 | Multifunctional compound 1 | 0.07 | 100 |  | 0.002 |  |  |  |
| Ex. B5 | Multifunctional compound 1 | 1.4 | 100 |  | 0.002 |  |  |  |
| Ex. B6 | Multifunctional compound 2 | 0.2 | 100 |  | 0.002 |  |  |  |
| Ex. B7 | Multifunctional compound 3 | 0.2 | 100 |  | 0.002 |  |  |  |
| Ex. B8 | Multifunctional compound 4 | 0.2 | 100 |  | 0.002 |  |  |  |
| Ex. B9 | Multifunctional compound 5 | 0.2 | 100 |  | 0.002 |  |  |  |
| Ex. B10 | Multifunctional compound 6 | 0.2 | 100 |  | 0.002 |  |  |  |
| Ex. B11 | Multifunctional compound 7 | 0.2 | 100 |  | 0.002 |  |  |  |
| Ex. B12 | Multifunctional compound 8 | 0.2 | 100 |  | 0.002 |  |  |  |
| Ex. B13 | Multifunctional compound 9 | 0.2 | 100 |  | 0.002 |  |  |  |
| Ex. B14 | Multifunctional compound 10 | 0.2 | 100 |  | 0.002 |  |  |  |
| Ex. B15 | Multifunctional compound 11 | 0.2 | 100 |  | 0.002 |  |  |  |
| Ex. B16 | Multifunctional compound 12 | 0.2 | 100 |  | 0.002 |  |  |  |

TABLE 2-continued

|  | Multifunctional compounds | | Aliphatic polyester resin | | | Flame retardant | | |
|---|---|---|---|---|---|---|---|---|
|  |  |  | Polylactic acid Terramac | Polyhydroxy alkanoate | Catalyst | Phosphorus-based | Sulfate-based APINON | Metal hydroxide ECOMAG |
|  | Type | Parts by mass | TE2000 Parts by mass | BIOPOLE Parts by mass | Tetrabutoxytitanium Parts by mass | PX200 Parts by mass | 901 Parts by mass | PZ-1 Parts by mass |
| Ex. B17 | Multifunctional compound 13 | 0.2 | 100 |  | 0.002 |  |  |  |
| Ex. B18 | Multifunctional compound 14 | 0.2 | 100 |  | 0.002 |  |  |  |
| Ex. B19 | Multifunctional compound 15 | 0.2 | 100 |  | 0.002 |  |  |  |
| Ex. B20 | Multifunctional compound 16 | 0.2 | 100 |  | 0.002 |  |  |  |

TABLE 3

|  | Multifunctional compound | | Aliphatic polyester resin | | | Flame retardant | | |
|---|---|---|---|---|---|---|---|---|
|  |  |  | Polylactic acid Terramac | Polyhydroxy alkanoate | Catalyst | Phosphorus-based | Sulfate-based APINON | Metal hydroxide ECOMAG |
|  | Type | Parts by mass | TE2000 Parts by mass | BIOPOLE Parts by mass | Tetrabutoxytitanium Parts by mass | PX200 Parts by mass | 901 Parts by mass | PZ-1 Parts by mass |
| Ex. B21 | Multifunctional compound 17 | 0.2 | 100 |  | 0.002 |  |  |  |
| Ex. B22 | Multifunctional compound 18 | 0.2 | 100 |  | 0.002 |  |  |  |
| Ex. B23 | Multifunctional compound 19 | 0.2 | 100 |  | 0.002 |  |  |  |
| Ex. B24 | Multifunctional compound 20 | 0.2 | 100 |  | 0.002 |  |  |  |
| Ex. B25 | Multifunctional compound 21 | 0.2 | 100 |  | 0.002 |  |  |  |
| Ex. B26 | Multifunctional compound 1 | 0.2 | 100 |  |  | 10 |  |  |
| Ex. B27 | Multifunctional compound 1 | 0.2 | 100 |  |  | 20 |  |  |
| Ex. B28 | Multifunctional compound 1 | 0.2 | 100 |  |  |  | 20 |  |
| Ex. B29 | Multifunctional compound 1 | 0.2 | 100 |  |  |  |  | 70 |
| Comp. Ex. B1 | Comparative compound 1 | 0.3 | 100 |  |  |  |  |  |
| Comp. Ex. B2 | Comparative compound 1 | 0.2 | 100 |  |  |  |  |  |
| Comp. Ex. B3 | Comparative compound 1 | 0.3 | 100 |  | 0.002 |  |  |  |
| Comp. Ex. B4 | Comparative compound 1 | 0.2 |  | 100 |  |  |  |  |
| Comp. Ex. B5 | Comparative compound 1 | 0.3 | 100 |  | 0.002 | 20 |  |  |
| Comp. Ex. B6 | Comparative compound 1 | 0.3 | 100 |  | 0.002 |  | 20 |  |
| Comp. Ex. B7 | Comparative compound 1 | 0.3 | 100 |  | 0.002 |  |  | 70 |

TABLE 4

| | | Evaluation | | | |
|---|---|---|---|---|---|
| | | Flame retardancy (UL-V) | | Hydrolysis resistance (65° C./95%) | |
| | End capping degree | Test specimens thickness 1.6 mm | Test specimens thickness 0.8 mm | Bending strength before being left to stand | Bending strength after being left to stand for 2000 hr |
| Ex. B1  | 0.51 | V-2 | V-2 | 72 | 64 |
| Ex. B2  | 0.92 | V-1 | V-2 | 58 | 58 |
| Ex. B3  | 0.89 | V-1 | V-2 | 59 | 58 |
| Ex. B4  | 0.88 | V-2 | V-2 | 58 | 59 |
| Ex. B5  | 0.9  | V-2 | V-2 | 57 | 58 |
| Ex. B6  | 0.91 | V-1 | V-2 | 55 | 55 |
| Ex. B7  | 0.92 | V-1 | V-2 | 60 | 59 |
| Ex. B8  | 0.88 | V-0 | V-1 | 62 | 60 |
| Ex. B9  | 0.89 | V-0 | V-1 | 62 | 60 |
| Ex. B10 | 0.86 | V-0 | V-1 | 60 | 59 |
| Ex. B11 | 0.92 | V-1 | V-2 | 58 | 58 |
| Ex. B12 | 0.94 | V-1 | V-2 | 54 | 55 |
| Ex. B13 | 0.93 | V-1 | V-2 | 56 | 55 |
| Ex. B14 | 0.92 | V-1 | V-2 | 54 | 55 |
| Ex. B15 | 0.91 | V-1 | V-2 | 55 | 55 |
| Ex. B16 | 0.91 | V-1 | V-2 | 58 | 56 |
| Ex. B17 | 0.9  | V-1 | V-2 | 57 | 58 |
| Ex. B18 | 0.92 | V-1 | V-2 | 54 | 54 |
| Ex. B19 | 0.92 | V-1 | V-2 | 55 | 54 |
| Ex. B20 | 0.91 | V-1 | V-2 | 57 | 56 |

TABLE 5

| | | Evaluation | | | |
|---|---|---|---|---|---|
| | | Flame retardancy (UL-V) | | Hydrolysis resistance (65° C./95%) | |
| | End capping degree | Test specimens (thickness of 1.6 mm) | Test specimens (thickness of 0.8 mm) | Bending strength before being left to stand | Bending strength after being left to stand for 2000 hr |
| Ex. B21 | 0.93 | V-1 | V-2 | 56 | 56 |
| Ex. B22 | 0.91 | V-1 | V-2 | 56 | 55 |
| Ex. B23 | 0.91 | V-1 | V-2 | 56 | 56 |
| Ex. B24 | 0.92 | V-1 | V-2 | 57 | 57 |
| Ex. B25 | 0.91 | V-2 | V-2 | 54 | 49 |
| Ex. B26 | 0.93 | V-0 | V-1 | 58 | 55 |
| Ex. B27 | 0.95 | V-0 | V-0 | 60 | 55 |
| Ex. B28 | 0.92 | V-0 | V-1 | 62 | 56 |
| Ex. B29 | 0.91 | V-0 | V-1 | 70 | 58 |
| Comp. Ex. B1 | 0.05 | Not-V | Not-V | 78 | 25 |
| Comp. Ex. B2 | 0.05 | Not-V | Not-V | 76 | 30 |
| Comp. Ex. B3 | 0.18 | Not-V | Not-V | 78 | 28 |
| Comp. Ex. B4 | 0.02 | Not-V | Not-V | 77 | 28 |
| Comp. Ex. B5 | 0.18 | V-2 | Not-V | 58 | 26 |
| Comp. Ex. B6 | 0.12 | V-2 | Not-V | 62 | 28 |
| Comp. Ex. B7 | 0.11 | Not-V | Not-V | 80 | 25 |

As can be seen from the results, Examples of the present invention exhibited superior flame retardancy and excellent hydrolysis resistance, as compared to Comparative Examples.

Example C

Examples C1 to C33 and Comparative Examples C1 to C5

The compositions shown in Tables 6 and 7 are mixed in a biaxial mixer (TEM58SS manufactured by Toshiba Machine Co., Ltd.) at a cylinder temperature of 180° C. to 200° C. to obtain a resin composition pellet.

In addition, in Tables 6 and 7, Comparative compound 1 is a lignophenol derivative obtained by a method described in Japanese Patent No. 3632763.

The obtained pellet is molded into ISO versatile dumbbell test specimens (corresponding to ISO527 tensile testing, corresponding to ISO178 bending test, test part thickness 4 mm, width 10 mm) and UL test specimens for UL-94 V testing (thickness: 0.8 mm, 1.6 mm) in an injection molding machine (NEX150 manufactured by Nissei Resin Industry Co., Ltd.) at a cylinder temperature of 180° C. to 200° C. at a molding temperature of 30° C.

(Evaluation)

The pellets and test specimens thus obtained are subjected to the following evaluation testing. The results thus obtained are shown in Tables 8 and 9.

—End Capping Degree—

An end capping degree of aliphatic polyester resin in the pellets is evaluated by FT-IR (JASCO, FT/IR-6000).

—Bending Elastic Modulus, Bending Fracture Distortion—

A bending elastic modulus and bending fracture distortion are measured by a measuring apparatus (INSTRON SV-50 manufactured by TOYO SEIKI Co., Ltd.) in accordance with the ISO178 bending test using ISO versatile dumbbell test specimens.

—Heat Deflection Temperature (HDT)—

A heat deflection temperature under a load of 1.8 MPa is measured with a HDT measuring apparatus (HDT-3 manufactured by TOYO SEIKI Co., Ltd.) in accordance with the ISO178 bending test using ISO versatile dumbbell test specimens.

—Flame Retardancy—

A UL-V testing is performed in accordance with UL-94 using UL test specimens for V testing. In addition, evaluation bases are V0, V1 and V2 from high flame retardancy in this order and in a case where flame retardancy is lower than V2, that is, the test specimen is combusted, the level is represented by V-Not.

TABLE 6

| | Multifunctional compound | | Aliphatic polyamide resin | | | | Catalyst Germanium oxide Parts by mass | Flame retardant | | |
|---|---|---|---|---|---|---|---|---|---|---|
| | | | Plant-based | | | Petroleum-based Polyamide 12 UBESTA Parts by mass | | Phosphorus-based PX200 Parts by mass | Sulfate-based APINON 901 Parts by mass | Metal hydroxide ECOMAG PZ-1 Parts by mass |
| | Types | Parts by mass | Polyamide 11 BMNO Parts by mass | Polyamide 10-10 ZYTEL RS10-10 Parts by mass | Polyamide 6-10 ZYTEL RS6-10 Parts by mass | | | | | |
| Ex. C1 | Multifunctional compound 1 | 2 | 100 | | | | | | | |
| Ex. C2 | Multifunctional compound 1 | 2 | 100 | | | | 0.04 | | | |
| Ex. C3 | Multifunctional compound 1 | 0.6 | 100 | | | | 0.04 | | | |
| Ex. C4 | Multifunctional compound 1 | 4.8 | 100 | | | | 0.04 | | | |
| Ex. C5 | Multifunctional compound 1 | 2 | | 100 | | | 0.04 | | | |
| Ex. C6 | Multifunctional compound 1 | 2 | | | 100 | | 0.04 | | | |
| Ex. C7 | Multifunctional compound 2 | 2 | 100 | | | | 0.04 | | | |
| Ex. C8 | Multifunctional compound 3 | 2 | 100 | | | | 0.04 | | | |
| Ex. C9 | Multifunctional compound 4 | 2 | 100 | | | | 0.04 | | | |
| Ex. C10 | Multifunctional compound 5 | 2 | 100 | | | | 0.04 | | | |
| Ex. C11 | Multifunctional compound 6 | 2 | 100 | | | | 0.04 | | | |
| Ex. C12 | Multifunctional compound 7 | 2 | 100 | | | | 0.04 | | | |
| Ex. C13 | Multifunctional compound 8 | 2 | 100 | | | | 0.04 | | | |
| Ex. C14 | Multifunctional compound 9 | 2 | 100 | | | | 0.04 | | | |
| Ex. C15 | Multifunctional compound 10 | 2 | 100 | | | | 0.04 | | | |
| Ex. C16 | Multifunctional compound 11 | 2 | 100 | | | | 0.04 | | | |
| Ex. C17 | Multifunctional compound 12 | 2 | 100 | | | | 0.04 | | | |
| Ex. C18 | Multifunctional compound 13 | 2 | 100 | | | | 0.04 | | | |
| Ex. C19 | Multifunctional compound 14 | 2 | 100 | | | | 0.04 | | | |
| Ex. C20 | Multifunctional compound 15 | 2 | 100 | | | | 0.04 | | | |

TABLE 7

| | Multifunctional compound | | Aliphatic polyamide resin | | | | Catalyst Germanium oxide Parts by mass | Flame retardant | | |
|---|---|---|---|---|---|---|---|---|---|---|
| | | | Plant-based | | | Petroleum-based Polyamide 12 UBESTA Parts by mass | | Phosphorus-based PX200 Parts by mass | Sulfate-based APINON 901 Parts by mass | Metal hydroxide ECOMAG PZ-1 Parts by mass |
| | Types | Parts by mass | Polyamide 11 BMNO Parts by mass | Polyamide 10-10 ZYTEL RS10-10 Parts by mass | Polyamide 6-10 ZYTEL RS6-10 Parts by mass | | | | | |
| Ex. C21 | Multifunctional compound 16 | 2 | 100 | | | | 0.04 | | | |
| Ex. C22 | Multifunctional compound 17 | 2 | 100 | | | | 0.04 | | | |
| Ex. C23 | Multifunctional compound 18 | 2 | 100 | | | | 0.04 | | | |
| Ex. C24 | Multifunctional compound 19 | 2 | 100 | | | | 0.04 | | | |

TABLE 7-continued

| | | Multifunctional compound | | Aliphatic polyamide resin | | | Catalyst Germanium | Flame retardant | | |
|---|---|---|---|---|---|---|---|---|---|---|
| | | | | Plant-based | | Petroleum-based | | Phosphorus-based | Sulfate-based | Metal hydroxide |
| | | | | Polyamide 11 | Polyamide 10-10 ZYTEL | Polyamide 6-10 ZYTEL | Polyamide 12 | | APINON | ECOMAG |
| | Types | | Parts by mass | BMNO Parts by mass | RS10-10 Parts by mass | RS6-10 Parts by mass | UBESTA Parts by mass | oxide Parts by mass | PX200 Parts by mass | 901 Parts by mass | PZ-1 Parts by mass |
| Ex. C25 | Multifunctional compound 20 | 2 | 100 | | | | 0.04 | | | |
| Ex. C26 | Multifunctional compound 21 | 2 | 100 | | | | 0.04 | | | |
| Ex. C27 | Multifunctional compound 1 | 2 | 100 | | | | 0.04 | 10 | | |
| Ex. C28 | Multifunctional compound 1 | 2 | 100 | | | | 0.04 | 20 | | |
| Ex. C29 | Multifunctional compound 1 | 2 | 100 | | | | 0.04 | | 20 | |
| Ex. C30 | Multifunctional compound 1 | 2 | 100 | | | | 0.04 | | | 70 |
| Ex. C31 | Multifunctional compound 1 | 0.4 | 100 | | | | 0.04 | | | |
| Ex. C32 | Multifunctional compound 1 | 5.5 | 100 | | | | 0.04 | | | |
| Ex. C33 | Multifunctional compound 1 | 2 | | | | 100 | 0.04 | | | |
| Comp. Ex. C1 | Comparative compound 1 | 2 | 100 | | | | 0.04 | | | |
| Comp. Ex. C2 | Comparative compound 1 | 2 | | 100 | | | 0.04 | | | |
| Comp. Ex. C3 | Comparative compound 1 | 2 | | | 100 | | 0.04 | | | |
| Comp. Ex. C4 | Comparative compound 1 | 2 | 100 | | | | 0.04 | 20 | | |
| Comp. Ex. C5 | Comparative compound 1 | 2 | 100 | | | | 0.04 | | | 70 |

TABLE 8

| | Evaluation | | | | |
|---|---|---|---|---|---|
| | End capping degree | Bending elastic modulus MPa | Bending fracture distortion % | Heat deflection temperature °C. | Flame retardancy (UL-V) |
| | | | | | Test specimens thickness 1.6 mm | Test specimens thickness 0.8 mm |
| Ex. C1 | 0.55 | 1950 | 12 | 72 | V-2 | V-2 |
| Ex. C2 | 0.91 | 2350 | 18 | 77 | V-0 | V-2 |
| Ex. C3 | 0.92 | 2200 | 15 | 70 | V-1 | V-2 |
| Ex. C4 | 0.91 | 2250 | 16 | 80 | V-0 | V-1 |
| Ex. C5 | 0.89 | 2350 | 14 | 74 | V-0 | V-1 |
| Ex. C6 | 0.88 | 2400 | 16 | 73 | V-0 | V-1 |
| Ex. C7 | 0.89 | 2250 | 18 | 75 | V-0 | V-1 |
| Ex. C8 | 0.91 | 2300 | 15 | 72 | V-0 | V-1 |
| Ex. C9 | 0.92 | 2150 | 16 | 74 | V-0 | V-1 |
| Ex. C10 | 0.91 | 2200 | 14 | 75 | V-0 | V-1 |
| Ex. C11 | 0.88 | 2450 | 15 | 72 | V-0 | V-1 |
| Ex. C12 | 0.92 | 2200 | 16 | 73 | V-0 | V-1 |
| Ex. C13 | 0.93 | 2250 | 16 | 72 | V-0 | V-1 |
| Ex. C14 | 0.92 | 2300 | 16 | 74 | V-0 | V-1 |
| Ex. C15 | 0.9 | 2500 | 12 | 76 | V-0 | V-1 |
| Ex. C16 | 0.89 | 2250 | 14 | 75 | V-0 | V-1 |
| Ex. C17 | 0.9 | 2400 | 13 | 74 | V-0 | V-1 |
| Ex. C18 | 0.92 | 2450 | 11 | 76 | V-0 | V-1 |
| Ex. C19 | 0.9 | 2500 | 12 | 76 | V-0 | V-1 |
| Ex. C20 | 0.89 | 2250 | 14 | 74 | V-0 | V-1 |

TABLE 9

| | Evaluation | | | | |
|---|---|---|---|---|---|
| | | Bending fracture distortion % | Heat deflection temperature ° C. | Flame retardancy (UL-V) | |
| | Bending elastic modulus MPa | | | Test specimens thickness 1.6 mm | Test specimens thickness 0.8 mm |
| | End capping degree | | | | |
| Ex. C21 | 0.88 | 2300 | 13 | 73 | V-0 | V-1 |
| Ex. C22 | 0.87 | 2250 | 15 | 75 | V-0 | V-1 |
| Ex. C23 | 0.91 | 2250 | 15 | 72 | V-0 | V-1 |
| Ex. C24 | 0.92 | 2300 | 16 | 72 | V-0 | V-1 |
| Ex. C25 | 0.89 | 2350 | 14 | 72 | V-0 | V-1 |
| Ex. C26 | 0.91 | 2050 | 9 | 75 | V-1 | V-2 |
| Ex. C27 | 0.94 | 2100 | 14 | 70 | V-0 | V-1 |
| Ex. C28 | 0.95 | 2000 | 16 | 68 | V-0 | V-0 |
| Ex. C29 | 0.93 | 2150 | 14 | 71 | V-0 | V-1 |
| Ex. C30 | 0.89 | 2650 | 10 | 76 | V-0 | V-1 |
| Ex. C31 | 0.78 | 1750 | 12 | 69 | V-0 | V-2 |
| Ex. C32 | 0.95 | 2800 | 7 | 82 | V-0 | V-1 |
| Ex. C33 | 0.92 | 1500 | 10 | 60 | V-2 | V-2 |
| Comp. Ex. C1 | 0.12 | 950 | 10 | 47 | Not-V | Not-V |
| Comp. Ex. C2 | 0.08 | 850 | 8 | 48 | Not-V | Not-V |
| Comp. Ex. C3 | 0.15 | 950 | 8 | 45 | Not-V | Not-V |
| Comp. Ex. C4 | 0.05 | 750 | 6 | 42 | Not-V | Not-V |
| Comp. Ex. C5 | 0.05 | 1000 | 4 | 55 | Not-V | Not-V |

Example D

Examples D1 to D31 and Comparative Examples D1 to D9

The compositions shown in Tables 10 and 11 are mixed in a biaxial mixer (TEM58SS manufactured by Toshiba Machine Co., Ltd.) at a cylinder temperature of 180° C. to 200° C. to obtain a resin composition pellet.

In addition, in Tables 10 and 11, Comparative compound 1 is a lignophenol derivative obtained by a method described in Japanese Patent No. 3632763.

The obtained pellet is molded into flat plate test specimens (50 mm×50 mm, thickness of 2 mm) and UL test specimens for UL-94 V testing (thickness: 0.8 mm, 1.6 mm) in an injection molding machine (NEX150 manufactured by Nissei Resin Industry Co., Ltd.) at a cylinder temperature of 180° C. to 200° C. at a molding temperature of 30° C.

(Evaluation)

The pellets and test specimens thus obtained are subjected to the following evaluation testing. The results thus obtained are shown in Tables 12 and 13.

—Molecular Weight Distribution—

The molecular weight distribution of pellets is measured using a GPC(HLC-9320 GPC manufactured by Tosoh cooperation).

—Dimensional Variation—

Dimensional variation is evaluated between before and after flat plate test specimens are left to stand under conditions of 60° C./85% RH for 500 hours.

In addition, the dimensional variation is obtained from calculation by measuring four sides of the flat plate in a longitudinal direction and a width direction and calculating differences therebetween before and after being left to stand.

—Steel Ball Drop Strength—

Flat plate test specimens are placed on a self-manufactured steel ball drop test apparatus, a steel ball having a diameter of 50 cm and a weight of 500 g is dropped, and the height at which cracks formed on the flat plate test specimens is measured.

—Flame Retardancy—

A UL-V testing is performed in accordance with UL-94 using UL test specimens for V testing. In addition, evaluation bases are V0, V1 and V2 from high flame retardancy in this order and in a case where flame retardancy is lower than V2, that is, the test specimen is combusted, the level is represented by V-Not.

TABLE 10

| | Multifunctional compound | | Cellulose | | | | | Flame retardant | | |
|---|---|---|---|---|---|---|---|---|---|---|
| | | | Diacetyl | Carboxymethyl | Cellulose acetate | Unsubstituted | Catalyst Manganese | Phosphorus-based | Sulfate-based APINON | Metal hydroxide ECOMAG |
| | Types | Parts by mass | cellulose Parts by mass | cellulose Parts by mass | propionate Parts by mass | cellulose Parts by mass | acetate Parts by mass | PX200 Parts by mass | 901 Parts by mass | PZ-1 Parts by mass |
| Ex. D1 | Multifunctional compound 1 | 5 | 100 | | | | | | | |
| Ex. D2 | Multifunctional compound 1 | 9.5 | 100 | | | | | 0.002 | | |
| Ex. D3 | Multifunctional compound 1 | 0.6 | 100 | | | | | 0.002 | | |
| Ex. D4 | Multifunctional compound 1 | 5 | 100 | | | | | 0.002 | | |
| Ex. D5 | Multifunctional compound 1 | 5 | | 100 | | | | 0.002 | | |
| Ex. D6 | Multifunctional compound 1 | 5 | | | 100 | | 0.002 | | | |

TABLE 10-continued

| | Multifunctional compound | | Cellulose | | | | Catalyst Manganese acetate Parts by mass | Flame retardant | | |
|---|---|---|---|---|---|---|---|---|---|---|
| | | | Diacetyl cellulose Parts by mass | Carboxymethyl cellulose Parts by mass | Cellulose acetate propionate Parts by mass | Unsubstituted cellulose Parts by mass | | Phosphorus-based PX200 Parts by mass | Sulfate-based APINON 901 Parts by mass | Metal hydroxide ECOMAG PZ-1 Parts by mass |
| | Types | Parts by mass | | | | | | | | |
| Ex. D7 | Multifunctional compound 1 | 5 | | | | 100 | 0.002 | | | |
| Ex. D8 | Multifunctional compound 2 | 5 | 100 | | | | 0.002 | | | |
| Ex. D9 | Multifunctional compound 3 | 5 | 100 | | | | 0.002 | | | |
| Ex. D10 | Multifunctional compound 4 | 5 | 100 | | | | 0.002 | | | |
| Ex. D11 | Multifunctional compound 5 | 5 | 100 | | | | 0.002 | | | |
| Ex. D12 | Multifunctional compound 6 | 5 | 100 | | | | 0.002 | | | |
| Ex. D13 | Multifunctional compound 7 | 5 | 100 | | | | 0.002 | | | |
| Ex. D14 | Multifunctional compound 8 | 5 | 100 | | | | 0.002 | | | |
| Ex. D15 | Multifunctional compound 9 | 5 | 100 | | | | 0.002 | | | |
| Ex. D16 | Multifunctional compound 10 | 5 | 100 | | | | 0.002 | | | |
| Ex. D17 | Multifunctional compound 11 | 5 | 100 | | | | 0.002 | | | |
| Ex. D18 | Multifunctional compound 12 | 5 | 100 | | | | 0.002 | | | |
| Ex. D19 | Multifunctional compound 13 | 5 | 100 | | | | 0.002 | | | |
| Ex. D20 | Multifunctional compound 14 | 5 | 100 | | | | 0.002 | | | |

TABLE 11

| | Multifunctional compound | | Cellulose | | | | Catalyst Manganese acetate Parts by mass | Flame retardant | | |
|---|---|---|---|---|---|---|---|---|---|---|
| | | | Diacetyl cellulose Parts by mass | Carboxymethyl cellulose Parts by mass | Cellulose acetate propionate Parts by mass | Unsubstituted cellulose Parts by mass | | Phosphorus-based PX200 Parts by mass | Sulfate-based APINON 901 Parts by mass | Metal hydroxide ECOMAG PZ-1 Parts by mass |
| | Types | Parts by mass | | | | | | | | |
| Ex. D21 | Multifunctional compound 15 | 5 | 100 | | | | 0.002 | | | |
| Ex. D22 | Multifunctional compound 16 | 5 | 100 | | | | 0.002 | | | |
| Ex. D23 | Multifunctional compound 17 | 5 | 100 | | | | 0.002 | | | |
| Ex. D24 | Multifunctional compound 18 | 5 | 100 | | | | 0.002 | | | |
| Ex. D25 | Multifunctional compound 19 | 5 | 100 | | | | 0.002 | | | |
| Ex. D26 | Multifunctional compound 20 | 5 | 100 | | | | 0.002 | | | |
| Ex. D27 | Multifunctional compound 21 | 5 | 100 | | | | 0.002 | | | |
| Ex. D28 | Multifunctional compound 1 | 5 | 100 | | | | 0.002 | 10 | | |
| Ex. D29 | Multifunctional compound 1 | 5 | 100 | | | | 0.002 | 20 | | |
| Ex. D30 | Multifunctional compound 1 | 5 | 100 | | | | 0.002 | | 10 | |
| Ex. D31 | Multifunctional compound 1 | 5 | 100 | | | | 0.002 | | | 50 |

TABLE 11-continued

| | Multifunctional compound | | Cellulose | | | | Catalyst Manganese acetate Parts by mass | Flame retardant | | |
|---|---|---|---|---|---|---|---|---|---|---|
| | | | Diacetyl | Carboxymethyl | Cellulose acetate | Unsubstituted | | Phosphorus-based | Sulfate-based APINON | Metal hydroxide ECOMAG |
| | Types | Parts by mass | cellulose Parts by mass | cellulose Parts by mass | propionate Parts by mass | cellulose Parts by mass | | PX200 Parts by mass | 901 Parts by mass | PZ-1 Parts by mass |
| Comp. Ex. D1 | Comparative compound 1 | 5 | 100 | | | | 0.002 | | | |
| Comp. Ex. D2 | Comparative compound 1 | 9.5 | 100 | | | | 0.002 | | | |
| Comp. Ex. D3 | Comparative compound 1 | 0.6 | 100 | | | | 0.002 | | | |
| Comp. Ex. D4 | Comparative compound 1 | 5 | | 100 | | | 0.002 | | | |
| Comp. Ex. D5 | Comparative compound 1 | 5 | | | 100 | | 0.002 | | | |
| Comp. Ex. D6 | Comparative compound 1 | 5 | | | | 100 | 0.002 | | | |
| Comp. Ex. D7 | Comparative compound 1 | 5 | 100 | | | | 0.002 | 10 | | |
| Comp. Ex. D8 | Comparative compound 1 | 5 | 100 | | | | 0.002 | | 10 | |
| Comp. Ex. D9 | Comparative compound 1 | 5 | 100 | | | | 0.002 | | | 50 |

TABLE 12

| | Evaluation | | | | |
|---|---|---|---|---|---|
| | | | Steel ball drop strength (height at | Flame retardant (UL-V) | |
| | Molecular weight distribution (Mw/Mn) | Dimensional variation % | which test specimen is cracked) mm | Test specimens (thickness 1.6 mm) | Test specimens (thickness 0.8 mm) |
| Ex. D1 | 2.8 | 0.14 | 800 | V-2 | V-2 |
| Ex. D2 | 7.8 | 0.05 | 2000 or more | V-1 | V-2 |
| Ex. D3 | 3.2 | 0.09 | 1500 | V-1 | V-2 |
| Ex. D4 | 4.3 | 0.08 | 1800 | V-1 | V-2 |
| Ex. D5 | 3.9 | 0.07 | 1700 | V-1 | V-2 |
| Ex. D6 | 4.8 | 0.06 | 1800 | V-1 | V-2 |
| Ex. D7 | 4.2 | 0.09 | 1600 | V-1 | V-2 |
| Ex. D8 | 3.9 | 0.05 | 1800 | V-1 | V-2 |
| Ex. D9 | 4.3 | 0.08 | 1700 | V-1 | V-2 |
| Ex. D10 | 4.6 | 0.07 | 1800 | V-1 | V-2 |
| Ex. D11 | 4.2 | 0.08 | 1600 | V-1 | V-2 |
| Ex. D12 | 4.3 | 0.09 | 1700 | V-1 | V-2 |
| Ex. D13 | 4.6 | 0.08 | 1800 | V-1 | V-2 |
| Ex. D14 | 5.1 | 0.07 | 1800 | V-1 | V-2 |
| Ex. D15 | 4.8 | 0.06 | 1800 | V-1 | V-2 |
| Ex. D16 | 4.2 | 0.08 | 1700 | V-1 | V-2 |
| Ex. D17 | 4.3 | 0.09 | 1800 | V-1 | V-2 |
| Ex. D18 | 3.9 | 0.08 | 1700 | V-1 | V-2 |
| Ex. D19 | 4.5 | 0.07 | 1800 | V-1 | V-2 |
| Ex. D20 | 4.7 | 0.07 | 1600 | V-1 | V-2 |

TABLE 13

| | Evaluation | | | | |
|---|---|---|---|---|---|
| | | | Steel ball drop strength (height at | Flame retardant (UL-V) | |
| | Molecular weight distribution (Mw/Mn) | Dimensional variation % | which test specimen is cracked) mm | Test specimens thickness 1.6 mm | Test specimens thickness 0.8 mm |
| Ex. D21 | 4.6 | 0.07 | 1800 | V-1 | V-2 |
| Ex. D22 | 4.5 | 0.08 | 1700 | V-1 | V-2 |
| Ex. D23 | 4.3 | 0.09 | 1800 | V-1 | V-2 |
| Ex. D24 | 4.5 | 0.08 | 1700 | V-1 | V-2 |
| Ex. D25 | 4.8 | 0.07 | 1800 | V-1 | V-2 |
| Ex. D26 | 4.6 | 0.07 | 1700 | V-1 | V-2 |
| Ex. D27 | 4.3 | 0.08 | 1600 | V-2 | V-2 |
| Ex. D28 | 3.9 | 0.09 | 1200 | V-0 | V-1 |
| Ex. D29 | 3.8 | 0.1 | 1000 | V-0 | V-0 |
| Ex. D30 | 4.2 | 0.08 | 1400 | V-0 | V-1 |
| Ex. D31 | 4.6 | 0.07 | 1200 | V-0 | V-1 |
| Comp. Ex. D1 | 4.3 | 0.24 | 200 or less | Not-V | Not-V |
| Comp. Ex. D2 | 7.6 | 0.21 | 200 or less | Not-V | Not-V |
| Comp. Ex. D3 | 2.3 | 0.28 | 200 or less | Not-V | Not-V |
| Comp. Ex. D4 | 4.2 | 0.25 | 200 or less | Not-V | Not-V |
| Comp. Ex. D5 | 4.1 | 0.26 | 200 or less | Not-V | Not-V |
| Comp. Ex. D6 | 4.3 | 0.24 | 200 or less | Not-V | Not-V |
| Comp. Ex. D7 | 3.9 | 0.31 | 200 or less | Not-V | Not-V |
| Comp. Ex. D8 | 4.1 | 0.29 | 200 or less | Not-V | Not-V |
| Comp. Ex. D9 | 4.3 | 0.22 | 200 or less | Not-V | Not-V |

As can be seen from the results, Examples of the present invention exhibited superior dimensional variation, steel ball drop strength and flame retardancy, as compared to Comparative Examples.

Here, the type of materials in the respective tables is described in detail.

—Aliphatic Polyester Resin—

Polylactic acid: "Terramac TE2000" manufactured by Unitika Ltd.

Polyhydroxy alkanoate: "Biopole" manufactured by Monsanto Co., Ltd. (Japan)

—Aliphatic Polyamide Resin—

Polyamide 11: "BMNO" manufactured by Arkema Co., Ltd.

Polyamide 10-10: "ZYTEL RS10-10" manufactured by DuPont Corp.

Polyamide 6-10: "ZYTEL RS6-10" manufactured by DuPont Corp.

Polyamide 12: "UBESTA" manufactured by UMG Co., Ltd.

—Cellulose Resin—

Diacetylcellulose: manufactured by Daicel Chemical Industries, Ltd.

Carboxymethyl cellulose: manufactured by Daicel Chemical Industries, Ltd.

Cellulose acetate propionate: manufactured by Eastman Kodak Company

Unsubstituted cellulose: manufactured by Daicel Chemical Industries, Ltd.

—Catalyst—

Tetrabutoxytitanium: manufactured by Wako Pure Chemical Industries Ltd.

Manganese acetate: manufactured by Wako Pure Chemical Industries Ltd.

—Flame Retardant—

Phosphorus-based flame retardant: "PX200" manufactured by DAIHACHI Chemical Industry Co., Ltd.

Sulfate-based flame retardant: "APINON 901" manufactured by SANWA Chemical Co., Ltd.

Metal hydroxide flame retardant: "ECOMAG PZ-1" manufactured by Tateho Chemical Industries Co., Ltd.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A compound represented by formula (1):

$$\left[HOR_3-O\right]_n \underset{\left[R_4OOC-O\right]_m}{\overset{}{\bigcirc}} \underset{O-R_1OH}{\overset{O}{\bigcirc}} \left[O-COOR_2\right]_l \quad (1)$$

wherein $R_1$ and $R_3$ each independently represent an alkylene group having 1 to 10 carbon atoms or an arylene group, $R_2$ and $R_4$ each independently represent a hydrogen atom, an alkyl group having 1 to 6 carbon atoms, or an aryl group; and l, n and m each independently represent a natural number of 1 to 3.

2. The compound according to claim 1, wherein the arylene group represented by $R_1$ and $R_3$ in formula (1) is one selected from a phenylene group and a naphthylene group.

3. The compound according to claim 1, wherein the alkyl group having 1 to 6 carbon atoms represented by $R_2$ and $R_4$ in formula (1) is one selected from a methyl group, an ethyl group, an n-propyl group, an isopropyl group, an n-butyl group, an isobutyl group, a sec-butyl group, a tert-butyl group, a pentyl group and a hexyl group.

4. The compound according to claim 1, wherein the aryl group represented by $R_2$ and $R_4$ in formula (1) is one selected from a phenyl group and a naphthyl group.

5. The compound according to claim 1, wherein the compound represented by formula (1) is the compound wherein $R_1$ represents an ethylene group or an n-butylene group, $R_3$ represents an ethylene group or an n-butylene group, $R_2$ represents a methyl group, $R_4$ represents a methyl group, l represents 1 or 2, n represents 1 or 2 and m represents 1 or 2.

6. A resin composition comprising a resin and a compound represented by formula (1):

$$\left[HOR_3-O\right]_n \underset{\left[R_4OOC-O\right]_m}{\overset{}{\bigcirc}} \underset{O-R_1OH}{\overset{O}{\bigcirc}} \left[O-COOR_2\right]_l \quad (1)$$

wherein $R_1$ and $R_3$ each independently represent an alkylene group having 1 to 10 carbon atoms or an arylene group, $R_2$ and $R_4$ each independently represent a hydrogen atom, an alkyl group having 1 to 6 carbon atoms, or an aryl group, and l, n and m each independently represent a natural number of 1 to 3.

7. The resin composition according to claim 6, wherein the arylene group represented by $R_1$ and $R_3$ in formula (1) is one selected from a phenylene group and a naphthylene group.

8. The resin composition according to claim 6, wherein the alkyl group having 1 to 6 carbon atoms represented by $R_2$ and $R_4$ in formula (1) is one selected from a methyl group, an ethyl group, an n-propyl group, an isopropyl group, an n-butyl group, an isobutyl group, a sec-butyl group, a tert-butyl group, a pentyl group and a hexyl group.

9. The resin composition according to claim 6, wherein the aryl group represented by $R_2$ and $R_4$ in formula (1) is one selected from a phenyl group and a naphthyl group.

10. The resin composition according to claim 6, wherein the compound represented by formula (1) is the compound wherein $R_1$ represents an ethylene group or an n-butylene group, $R_3$ represents an ethylene group or an n-butylene group, $R_2$ represents a methyl group, $R_4$ represents a methyl group, l represents 1 or 2, n represents 1 or 2 and m represents 1 or 2.

11. The resin composition according to claim 6, wherein the resin is an aliphatic polyester resin.

12. The resin composition according to claim 6, wherein the resin is an aliphatic polyimide resin.

13. The resin composition according to claim 6, wherein the resin is a cellulose resin.

14. A resin molded article comprising a resin and 1 compound represented by formula (1):

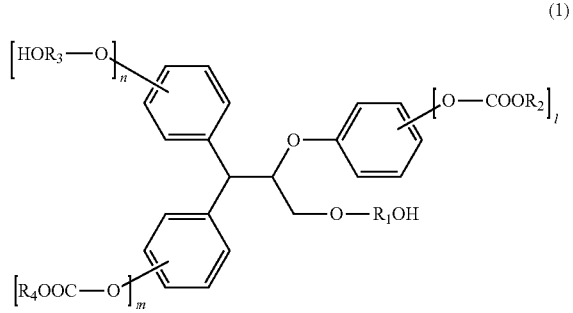

(1)

wherein $R_1$ and $R_3$ each independently represent an alkylene group having 1 to 10 carbon atoms or an arylene group, $R_2$ and $R_4$ each independently represent a hydrogen atom, an alkyl group having 1 to 6 carbon atoms, or an aryl group, and l, n and m each independently represent a natural number of 1 to 3.

15. The resin molded article according to claim 14, wherein the arylene group represented by $R_1$ and $R_3$ in formula (1) is one selected from a phenylene group and a naphthylene group.

16. The resin molded article according to claim 14, wherein the alkyl group having 1 to 6 carbon atoms represented by $R_2$ and $R_4$ in formula (1) is one selected from a methyl group, an ethyl group, an n-propyl group, an isopropyl group, an n-butyl group, an isobutyl group, a sec-butyl group, a tert-butyl group, a pentyl group and a hexyl group.

17. The resin molded article according to claim 14, wherein the aryl group represented by $R_2$ and $R_4$ in formula (1) is one selected from a phenyl group and a naphthyl group.

18. The resin molded article according to claim 14, wherein the compound represented by formula (1) is the compound wherein $R_1$ represents an ethylene group or an n-butylene group, $R_3$ represents an ethylene group or an n-butylene group, $R_2$ represents a methyl group, $R_4$ represents a methyl group, l represents 1 or 2, n represents 1 or 2 and m represents 1 or 2.

* * * * *